United States Patent [19]

Fahey

[11] 4,055,582
[45] Oct. 25, 1977

[54] SYNTHESIS OF NICKEL AND PALLADIUM ORGANOPHOSPHORUS COMPLEXES

[75] Inventor: Darryl R. Fahey, Bartlesville, Okla.

[73] Assignee: Phillips Petroleum Company, Bartlesville, Okla.

[21] Appl. No.: 684,986

[22] Filed: May 10, 1976

[51] Int. Cl.$^2$ .................. C07F 15/04; C07F 15/00
[52] U.S. Cl. .................. 260/439 R; 252/431 P; 260/666 B; 260/683.15 D
[58] Field of Search .................. 260/439 R, 429 R

[56] References Cited

U.S. PATENT DOCUMENTS

| | | | |
|---|---|---|---|
| 3,102,899 | 9/1963 | Cannell | 260/439 R |
| 3,519,663 | 7/1970 | O'Brien et al. | 260/439 R X |
| 3,671,560 | 6/1972 | Fahey | 260/429 R |
| 3,776,929 | 12/1973 | Mrowca | 260/429 R |
| 3,799,961 | 3/1974 | Varshavsky | 260/429 R |
| 3,808,246 | 4/1974 | Fahey | 260/439 R |
| 3,818,063 | 6/1974 | Fahey | 260/439 R |
| 3,891,684 | 6/1975 | Jung | 260/429 R |

FOREIGN PATENT DOCUMENTS 1,000,477   8/1965   United Kingdom

OTHER PUBLICATIONS

Cundy, J. Organometal. Chem. 69, pp. 305-310 (1974).
Issleib et al., Ber. 95, pp. 2742-2746 (1962).
Tolman, J.A.C.S. 92 (10), pp. 2956-2965 (1970).
Parshall, J.A.C.S. 96 (8), pp. 2360-2365 (1974).
Chatt et al., J. Chem. Soc. Part II, pp. 1718-1729 (1960).
Issleib, L. Fur Chem. "Zur Reaklivitat P-substituierter Alkali phosphide" v.2, pp. 168-169 (1962).

*Primary Examiner*—Helen M. S. Sneed

[57] ABSTRACT

A process is disclosed comprising reacting at least one compound of the formula $RMX(PR_3)_2$ and at least one compound of the formula $APR_2$ to produce at least one composition which can be represented by the formula $M(PQ_3)_n$, wherein M is palladium or nickel; X is a halogen; A is an alkali metal; each R is individually selected from the group consisting of suitable aliphatic hydrocarbyl radicals, halosubstituted aliphatic hydrocarbyl radicals, aromatic hydrocarbyl radicals wherein at least one carbon adjacent the radical carbon has a hydrogen substituent, halosubstituted aromatic hydrocarbyl radicals wherein at least one carbon adjacent the radical carbon has a hydrogen substituent, hydrocarbyloxy radicals, and halosubstituted hydrocarbyloxy radicals, each Q is individually selected from any R contained in the reactants; each $PR_3$ may be the same or different; each $PQ_3$ may be the same or different; the molar ratio of each different $PQ_3$ to M can be any rational number such that the sum of the molar ratios of the different $PQ_3$'s equals n; and n equals 3 when M is palladium or 4 when M is nickel.

26 Claims, No Drawings

SYNTHESIS OF NICKEL AND PALLADIUM ORGANOPHOSPHORUS COMPLEXES

This invention relates to the preparation of organophosphorus-containing complexes of nickel or palladium.

It is known that various organophosphorus complexes of nickel or palladium have a catalytic effect upon a variety of organic transformations; examples include olefin oligomerizations, diene oligomerizations, alkyne/diene co-oligomerizations, and alkene/diene co-oligomerizations.

An object of the present invention is to provide a new method for preparing organophosphorus complexes of nickel or palladium.

Another object of the present invention is to provide a new method for preparing tris(triethylphosphine)(triphenylphosphine) nickel.

A further object is to provide a new method for preparing tetrakis(triphenylphosphine) nickel.

A still further object is to provide a process for producing a palladium composition having about 1.9 moles of triethylphosphine and about 1.1 moles of triphenylphosphine for every mole of palladium.

A further object is to provide such a palladium composition.

In accordance with the present invention at least one compound of the formula $RMX(PR_3)_2$ is reacted with at least one compound of the formula $APR_2$ in the presence of a suitable diluent under reaction conditions sufficient to produce at least one composition which can be represented by the formula $M(PQ_3)_n$ wherein M is palladium or nickel; X is a halogen; A is an alkali metal; each R is individually selected from the group consisting of suitable aliphatic hydrocarbyl radicals, halosubstituted aliphatic hydrocarbyl radicals, aromatic hydrocarbyl radicals wherein at least one carbon adjacent the radical carbon has a hydrogen substituent, halosubstituted aromatic hydrocarbyl radicals wherein at least one carbon adjacent the radical carbon has a hydrogen substituent, hydrocarbyloxy radicals, and halosubstituted hydrocarbyloxy radicals, each Q is individually selected from any R contained in the reactants; each $PR_3$ may be the same or different; each $PQ_3$ may be the same or different; the molar ratio of each different $PQ_3$ to M can be any rational number such that the sum of the molar ratios of the different $PQ_3$'s equals $n$; and $n$ equals 3 when M is palladium or 4 when M is nickel.

An optional embodiment of the present invention involves employing an additional reactant consisting of at least one phosphorus-containing compound of the formula $PR_3$ where R is as described for $RMX(PR_3)_2$ and $APR_2$.

Examples of R radicals suitable for the three reactants include alkyl, aryl wherein at least one carbon adjacent the radical carbon has a hydrogen substituent, alkoxy, aryloxy, alkenyl, alkynyl, haloalkyl, haloaryl wherein at least one carbon adjacent the radical carbon has a hydrogen substituent, alkaryl, aralkyl, alkadienyl, and the like. The preferred R radicals are those containing 1 to 12 carbon atoms. In one preferred embodiment each R is individually selected from the group consisting of alkyl or aryl radicals.

In the preceding description of the R radicals the term "radical carbon" is used to denote the carbon of the radical that is bonded to nickel, palladium, or phosphorus in the respective compounds of the formulas $RMX(PR_3)_2$, $APR_2$, and $PR_3$. For example, if $RMX(PR_3)_2$ is bromo(o-tolyl)bis(triphenylphosphine)nickel the "radical carbon" of each radical is the carbon bonded to the phosphorus and the "radical carbon" of the o-tolyl radical is the carbon bonded to the nickel.

Examples of typical compounds of the formula $RMX(PR_3)_2$, as above defined, include bromo(phenyl)bis(triethylphosphine)palladium or nickel, chloro(phenyl)bis(triethylphosphine)palladium or nickel, iodo(phenyl)bis(triethylphosphine)palladium or nickel, bromo(phenyl)bis(triphenylphosphine)palladium or nickel, bromo(ethyl)bis(diethylethoxyphosphine)nickel or palladium, bromo(dodecyl)bis(dibutylphenylphosphine)nickel or palladium, bromo(3-chlorophenyl)bis(dimethyltrifluoromethylphosphine)nickel or palladium, chloro(phenyl)bis(methoxymethylbutylphosphine)nickel or palladium, bromo(chlorophenyl)(dimethylphenylphosphine)(triethylphosphine)nickel or palladium, chloro(phenyl)bis(trimethoxyphosphine)nickel or palladium [which more commonly would be called chloro(phenyl)bis(trimethylphosphite)nickel or palladium], bromo(ethyl)bis(triphenylphosphine)nickel or palladium and the like.

Examples of typical compounds of the formula $APR_2$, as above defined, include lithium diphenylphosphide, sodium diethylphosphide, potassium(ethyl)(methoxy)phosphide, lithium(dodecyl)(phenyl)phosphide, sodium(dichlorophenyl)(phenyl)phosphide, and the like. It is preferred that each compound $APR_2$ be employed in the form of an etherate, for example, a diethyl etherate. Of course other suitable etherates can also be employed.

The organophosphorus nickel and palladium complexes prepared according to this invention, as well as many of the compounds employed in their preparation, are sensitive to oxygen and/or water to varying degrees. Therefore the preparation of the complexes should be conducted under an inert atmosphere, for example in a recirculating-atmosphere drybox providing an argon atmosphere.

According to this invention any diluent can be employed that does not prevent the formation of the desired product. Suitable diluents include, for example, unsubstituted ethers, aromatic hydrocarbons, aliphatic hydrocarbons, and mixtures of two or more thereof. Typical specific examples of diluents include diethyl ether, p-dioxane, tetrahydrofuran, m-dioxane, 1,2-dimethoxyethane, benzene, toluene, pentane, hexane, octane, and mixtures of two or more thereof. Preferred diluents include cyclic or acylic ethers or admixtures of at least one such ether with at least one hydrocarbon containing 5 to 10 carbon atoms.

Although any suitable temperature can be employed for the contacting of reactants according to this invention, generally the temperature should be in the range of about $-50°$ to about $200°$ C, and preferably will be in the range of about $-10°$ to about $60°$ C. Generally any pressure is satisfactory that will essentially maintain the diluent in the liquid phase at the temperature employed. Thus atmospheric pressure is suitable for the practice of the instant invention wherein the reaction temperature does not exceed the boiling point of the diluent. When the reaction temperature exceeds the normal boiling point of the solvent, the pressure in the system should approximate the vapor pressure of the solvent at that temperature. Of course, for convenience, atmospheric pressure is preferred and thus preferably diluents and temperature conditions are selected accordingly.

The reaction time will of course depend upon the reaction conditions employed and the extent of conversion that is desired. Generally, the reaction time will be in the range of about 0.1 to about 100 hours, preferably about 0.5 to about 6 hours.

While the molar ratio of the reactants can affect the yield it is not considered to be critical. The molar ratio of total $APR_2$ to total $RMX(PR_3)_2$ is generally in the range of about 0.5:1 to about 1.5:1, preferably in the range of about 0.8:1 to about 1.2:1. When $PR_3$ is also employed as a reactant the molar ratio of total $PR_3$ to total $RMX(PR_3)_2$ is generally in the range of about 0.5:1 to about 1.5:1, preferably about 0.8:1 to about 1.2:1.

The products produced according to this invention can be recovered and purified using techniques conventionally employed by those skilled in the art for recovering and purifying products contained in a diluent. For this reason, it is preferable that a diluent be employed in which the product is at least relatively insoluble at a temperature in the range of about $-20°$ to about $-80°$ C. Alternatively to enable isolation of product by evaporating the reaction mixture in vacuo it is advantageous to employ a diluent that is sufficiently volatile.

The formula $M(PQ_3)_n$, as above defined, includes known palladium and nickel complexes as well as heretofore unknown palladium and nickel complexes. Any of the previously unknown products can be substituted for similar nickel or palladium complexes conventionally used as catalysts for organic transformations. For example, a composition of the formula $Pd(triethylphosphine)_{1.9}$-(triphenylphosphine)$_{1.1}$ can be employed as an olefin oligomerization catalyst. Also the products of this invention can be employed as intermediates to other palladium or nickel compositions that have various uses. For example, the present invention can be employed to produce tris(triethylphosphine)(triphenylphosphine) nickel which can be converted to bis($\mu$-diphenylphosphido)tris(triethylphosphine)dinickel which has utility, when activated by an organoaluminum halide, as an alkene oligomerization catalyst.

Without further elaboration one skilled in the art using the preceding disclosure should be able to utilize the present invention to its fullest extent. The following preferred specific embodiments are, therefore, to be constituted as merely illustrative and not unduly limitative of the remainder of the specification and claims in any way whatsoever.

In the following examples the work described was done at atmospheric pressure in a recirculating-atmosphere drybox providing an argon atmosphere.

EXAMPLE I

A solution of 0.45 g (1.0 mmol) of trans-bromo(phenyl)bis(triethylphosphine)nickel(II) in 5 ml of diethyl ether and 0.27 g (1.0 mmol) of lithium diphenylphosphide diethyl etherate in 5 ml of diethyl ether were combined at 0° C. The mixture immediately turned brown and on cooling to $-78°$ C a precipitate formed and was recovered by suction filtration. About 0.12 g of orange crystals having a melting point of 93°–94° C were recovered. The composition of the product was substantiated by infrared and elemental analyses as being tris(triethylphosphine)(triphenylphosphine)-nickel. The yield was thus 18 percent of theoretical.

EXAMPLE II

A solution of 0.54 g (2.0 mmols) of lithium diphenylphosphide diethyl etherate and 0.24 g (2.0 mmols) of triethylphosphine in 7 ml of diethyl ether was quickly added to 0.90 g (2.0 mmols) of trans-bromo(phenyl)bis(triethylphosphine)nickel(II) in 5 ml of diethyl ether at about 0° C. The solution immediately turned dark brown and on cooling to $-72°$ C the solution gradually became green and a solid precipitated. The precipitated crystals were recovered by suction filtration, washed with cold ether and dried in vacuo to give 1.0 g (74% of theory) of orange crystalline tris(triethylphosphine)(triphenylphosphine)nickel(0) with a melting point of 94°–95° C. The infrared spectrum of this product was consistent with the composition $Ni(PEt_3)_3$-$(PPh_3)$. This example demonstrates that greater yields are obtained if triethylphosphine is employed in the reaction.

EXAMPLE III

A solution of 1.06 g (4.0 mmols) of lithium diphenylphosphide diethyl etherate in 10 ml of diethyl ether was added to a stirred solution of 2.0 g (4.0 mmols) of trans-bromo(phenyl)bis(triethylphosphine)palladium(II) in 10 ml of diethyl ether at 0° C. The solution turned dark brown and on cooling to $-72°$ C a golden precipitate formed and was removed by suction filtration to yield 0.77 g of product. The formula that comes closest to fitting the carbon-hydrogen analysis on this product is $Pd(PPh_3)_{1.1}(PEt_3)_{1.9}$; calculated analysis: wt. % C, 60.50; wt. % H, 7.32; observed analysis: wt. % C, 60.11; wt. % H, 6.60.

EXAMPLE IV

Preparation of $Ni_2(\mu-PPh_2)_2(PEt_3)_3$ from $Ni(PEt_3)_3(PPh_3)$

A closed vial containing 1.36 g (2.0 mmol) of tris(triethylphosphine)(triphenylphosphine)nickel(0) having the formula $Ni(PEt_3)_3(PPh_3)$, in 20 ml of hexane was suspended in a refluxing benzene bath. In less than about 10 minutes the orange colored solution had turned dark green. After 5 hours the solution was cooled to $-78°$ C and lustrous dark green crystals precipitated. The crystals were removed by suction filration, washed with cold hexane, and dried in a stream of argon to yield 0.39 g (0.46 mmol) of $Ni_2(\mu-PPh_2)_2(PEt_3)_3$; m.p. 193°–195° C (dec.); ir (Nujol) 3040 w, 2910 vs, 2880 vs, 1580 m, 1455 s, 1425 m, 1375 m, 1150 w, 1075 w, 1055 w, 1030 s, 1000 w, 767 s, 763 s, 748 ms, 736 s, 724 m, 707 s, 700 vs, 694 s cm$^{-1}$; NMR ($C_6D_6$) $\delta$ 7.9 (v br, 6.6), 7.15 (v br, 17.4 — includes $C_6D_5H$ impurity), 1.00 (v br, 45).

Anal. Calcd. for $C_{42}H_{65}Ni_2P_5$: C, 59.89; H, 7.78; Ni, 13.94. Found: C, 59.54; H, 7.78; Ni, 13.88.

EXAMPLE V

Monoolefin Oligomerization Employing $Ni_2(\mu-PPh_2)_2(PEt)_3)_3$

A predried nine ounce beverage bottle equipped with a magnetic stirring bar was charged in a dry box with 0.04 g (0.05 mmol) of $Ni_2(\mu-PPh_2)_2)(PEt_3)_3$, 20 ml of chlorobenzene and then capped. The capped bottle was removed from the dry box and flushed successively for one hour periods, with argon and propylene before chilling the stirred solution for 5 minutes in an ice-salt-water bath. The chilled bottle was pressured to 30 psig with propylene and then vented to 5 psig. A 0.70 ml (equivalent to 0.70 mmol methylaluminum sesquichloride) aliquot of a 1 molar solution of methylaluminum sesquichloride in chlorobenzene was added by syringe and the solution immediately turned from green to brown. The pressure was increased to 30 psig with propylene and maintained at this pressure in the cold bath and one hour later the propylene was shut off, the bottle vented and 10 ml of saturated aqueous sodium chloride solution was added. The aqueous phase was separated, extracted with 5 ml of chlorobenzene and the chlorobenzene extract was combined with the chlorobenzene phase from the reaction mixture. The combined chlorobenzene phases were dried over anhydrous magnesium sulfate, filtered and distilled to recover 43.4 g of propylene dimers collected over the temperature range of 60°-68° C.

Skeletal characterization of the propylene dimers was carried out by hydrogenating a 2.0 g sample of the above isolated propylene dimers over 0.1 g of platinum oxides under 50-90 psig of hydrogen for a period of 3 hours. The hydrogenated product mixture was analyzed by gas-liquid partition chromatography on a 20 ft. by 0.125 in. isoquinoline column at a 25° C oven temperature. The composition in area percent of the hydrogenated product was as follows: 19% 2,3-dimethylbutane, 68% 2-methylpentane and 13% n-hexane.

From the foregoing examples and description, one skilled in the art can easily ascertain the essential characteristics of this invention and without departing from the spirit and scope thereof, can make various changes and modifications to adapt it to various usages and conditions. Consequently, such obvious changes and modifications, should be within the range of equivalence of the following claims.

What is claimed is:

1. A process comprising reacting at least one compound of the formula $RMX(PR_3)_2$ with at least one compound of the formula $APR_2$ in the presence of a diluent under reaction conditions sufficient to produce at least one composition which can be represented by the formula $M(PQ_3)_n$, wherein M is palladium or nickel; X is a halogen; A is an alkali metal; each R is individually selected from the group consisting of suitable aliphatic hydrocarbyl radicals, halosubstituted aliphatic hydrocarbyl radicals, aromatic hydrocarbyl radicals wherein at least one carbon adjacent the radical carbon has a hydrogen substituent, halosubstituted aromatic hydrocarbyl radicals wherein at least one carbon adjacent the radical carbon has a hydrogen substituent, hydrocarbyloxy radicals, and halosubstituted hydrocarbyloxy radicals, each Q is individually selected from any R contained in the reactants; each $PR_3$ may be the same or different; each $PQ_3$ may be the same or different; the molar ratio of each different $PQ_3$ to M can be any rational number such that the sum of the molar ratios of the different $PQ_3$'s equals n; and n equals 3 when M is palladium or 4 when M is nickel.

2. A process according to claim 1 wherein each R contains 1 to 12 carbon atoms.

3. A process according to claim 2 wherein each R is individually selected from the group consisting of alkyl, aryl wherein at least one carbon adjacent the radical carbon has a hydrogen substituent, alkoxy, aryloxy, alkaryl, alkynyl, haloalkyl, haloaryl wherein at least one carbon adjacent the radical carbon has a hydrogen substituent, alkaryl, aralkyl, and alkadienyl radicals.

4. A process according to claim 2 wherein the molar ratio of $APR_2$ to $RMX(PR_3)_2$ is in the range of about 0.5:1 to about 1.5:1, the temperature is in the range of about −50° to about 200° C an the pressure is such that the diluent is essentially maintained in the liquid phase.

5. A method according to claim 4 wherein M is nickel and each said $APR_2$ is employed in the form of an etherate.

6. A method according to claim 5 wherein at least one transhalo(phenyl)bis(triethylphosphine)nickel(II) is reacted with at least one alkali metal diphenylphosphide diethyl etherate.

7. A method according to claim 6 wherein transbromo(phenyl)bis(triethylphosphine)nickel(II) is reacted with an alkali metal diphenylphosphide diethyl etherate.

8. A method according to claim 7 wherein the alkali metal of the alkali metal diphenylphosphide diethyl etherate is lithium.

9. A method according to claim 8 wherein the molar ratio of transbromo(phenyl)bis(triethylphosphine)nickel(II) to lithium diphenylphosphide diethyl etherate is about 1:1, the temperature is about 0° C, and the reaction is conducted under an atmosphere of inert gas.

10. A method according to claim 9 wherein tris(triethylphosphine)(triphenylphosphine)nickel is produced and recovered.

11. A method according to claim 5 wherein at least one compound of the formula $PR_3$ is also included as a reactant, wherein each R is individually selected from the group consisting of suitable aliphatic hydrocarbyl radicals, halosubstituted aliphatic hydrocargyl radicals, aromatic hydrocarbyl radicals wherein at least one carbon adjacent the radical carbon has a hydrogen substituent, halosubstituted aromatic hydrocarbyl radicals wherein at least one carbon adjacent the radical carbon has a hydrogen substituent, hydrocarbyloxy radicals, and halosubstituted hydrocarbyloxy radicals, said radicals having 1 to 12 carbon atoms.

12. A method according to claim 11 wherein each R is individually selected from the group consisting of alkyl or aryl radicals.

13. A method according to claim 12 wherein the molar ratio of $PR_3$ to said $RMX(PR_3)_2$ is in the range of about 0.5:1 to about 1.5:1.

14. A method according to claim 13 wherein at least one transhalo(phenyl)bis(triethylphosphine)nickel(II) and at least one alkali metal diphenylphosphide etherate are reacted in the presence of triethylphosphine.

15. A method according to claim 14 wherein transbromo(phenyl)bis(triethylphosphine)nickel(II) and lithium diphenylphosphide diethyl etherate are reacted in the presence of triethylphosphine at a temperature of about 0° C under an atmosphere of inert gas.

16. A method according to claim 15 wherein tris(triethylphosphine)(triphenylphosphine)nickel(0) is produced and recovered.

17. A method according to claim 13 wherein at least one transhalo(phenyl)bis(triphenylphosphine)nickel(II) and at least one alkali metal diphenylphosphide etherate are reacted in the presence of triphenylphosphine.

18. A method according to claim 17 wherein transbromo(phenyl)bis(triphenylphosphine)nickel(II) and lithium diphenylphosphide diethyl etherate are reacted in the presence of triphenylphosphine at a temperature of about 0° C under an atmosphere of inert gas.

19. A method according to claim 18 wherein tetrakis(triphenylphosphine)nickel(0) is produced and recovered.

20. A method according to claim 5 wherein each R is individually selected from the group consisting of alkyl or aryl radicals.

21. A method according to claim 4 wherein M is palladium and each said $APR_2$ is employed in the form of an etherate.

22. A method according to claim 21 wherein at least one transhalo(phenyl)bis(triethylphosphine)palladium-(II) is reacted with at least one alkali metal diphenylphosphide diethyl etherate.

23. A method according to claim 22 wherein trans-bromo(phenyl)bis(triethylphosphine)palladium(II) is reacted with an alkali metal diphenylphosphide diethyl etherate.

24. A method according to claim 23 wherein the alkali metal of the alkali metal diphenylphosphide diethyl etherate is lithium.

25. A method according to claim 24 wherein the temperature is about 0° C, the reaction is conducted under an atmosphere of inert gas, and a composition of the formula $Pd(PEt_3)_{1.9}(PPh_3)_{1.1}$ is produced and recovered wherein $PEt_3$ is triethylphosphine and $PPh_3$ is triphenylphosphine.

26. A composition of matter having the average formula of $Pd(PEt_3)_{1.9}(PPh_3)_{1.1}$ wherein $PEt_3$ is triethylphosphine and $PPh_3$ is triphenylphosphine.

* * * * *